US011793750B2

(12) United States Patent
Chowdary

(10) Patent No.: US 11,793,750 B2
(45) Date of Patent: Oct. 24, 2023

(54) SUSTAINED RELEASE ESTROGEN VAGINAL RING PESSARY FOR TREATMENT OF ATROPHY, CYSTITIS AND UTEROVAGINAL PROLAPSE

(71) Applicant: Prathima Chowdary, Birkenhead (NZ)

(72) Inventor: Prathima Chowdary, Birkenhead (NZ)

( * ) Notice: Subject to any disclaimer, the term of this patent is extended or adjusted under 35 U.S.C. 154(b) by 0 days.

(21) Appl. No.: 17/829,702

(22) Filed: Jun. 1, 2022

(65) Prior Publication Data

US 2022/0287960 A1 Sep. 15, 2022

Related U.S. Application Data

(63) Continuation of application No. PCT/IB2020/061497, filed on Dec. 4, 2020.

(30) Foreign Application Priority Data

Dec. 6, 2019 (IN) .............................. 201941050413

(51) Int. Cl.
*A61K 9/00* (2006.01)
*A61K 31/565* (2006.01)
(Continued)

(52) U.S. Cl.
CPC .......... *A61K 9/0036* (2013.01); *A61K 31/565* (2013.01); *A61K 31/566* (2013.01); *A61K 47/34* (2013.01)

(58) Field of Classification Search
None
See application file for complete search history.

(56) References Cited

U.S. PATENT DOCUMENTS

2007/0178133 A1 8/2007 Rolland
2007/0254014 A1 11/2007 Ahmed et al.
(Continued)

FOREIGN PATENT DOCUMENTS

CN 109248139 A 1/2019
CN 104546668 B 3/2019
(Continued)

OTHER PUBLICATIONS

Eriksen, "A randomized, open, parallel-group study on the preventive effect of an estradiol-releasing vaginal ring (Estring) on recurrent urinary tract infections in postmenopausal women" Am J Obstet Gynecol 1999;180:1072-9, p. 1073, left col. para 2, abstract, Figure 1, Table 2, p. 2,6,11 1073, right col., para 4.
(Continued)

*Primary Examiner* — Patricia Duffy
*Assistant Examiner* — Garen Gotfredson
(74) *Attorney, Agent, or Firm* — INNOVATION CAPITAL LAW GROUP, LLP; Vic Lin

(57) ABSTRACT

The present invention relates to devices and methods for treating prolapsed pelvic organ, cystitis and Atrophy in women. Particularly, the invention relates to drug loaded vaginal support devices and methods wherein the device is inserted in vagina to support as well as release the drug. Specifically the invention relates to a Vaginal Ring Pessary comprising Estrogen in Silicone rubber polymer matrix, which releases drug over a prolonged period of about 180 days. Additionally the invention relates to the method of fabrication of the device and its use in treatment of vaginal atrophy, cystitis and uterovaginal prolapse.

11 Claims, 8 Drawing Sheets

(51) Int. Cl.
*A61K 31/566* (2006.01)
*A61K 47/34* (2017.01)

(56) References Cited

U.S. PATENT DOCUMENTS

| | | |
|---|---|---|
| 2010/0087402 A1 | 4/2010 | Wang et al. |
| 2015/0004214 A1 | 1/2015 | Garcia et al. |
| 2016/0250229 A1* | 9/2016 | Campos Perez ..... A61K 31/573 514/181 |
| 2019/0358243 A1 | 11/2019 | Mirkin et al. |

FOREIGN PATENT DOCUMENTS

| | | |
|---|---|---|
| EP | 0253109 B1 | 10/1991 |
| EP | 2799042 A4 | 2/2015 |
| EP | 3501543 A1 | 6/2019 |
| WO | 9922680 A1 | 5/1999 |
| WO | 2012024461 A2 | 2/2012 |
| WO | 2015073177 | 7/2016 |

OTHER PUBLICATIONS

International Preliminary Report on Patentability (Chapter II) dated Oct. 20, 2021 from PCT Application No. PCT/IB2020/061497, 34 pages.
International Search Report & Written Opinion dated Jul. 21, 2021 from PCT Application No. PCT/IB2020/061497, 11 pages.
Nusil, "MED-4870" Nov. 28, 2018, pp. 1-3 entire document especially p. 1, para 1-2, Table 1.
Warren et al. "Urinary Tract Infection and Inflammation at Onset of Interstitial Cystitis/Painful Bladder Syndrome" Female Urology, 2007, pp. 1085-1090, entire document especially p. 1089, left col., para 1.

* cited by examiner

SUSTAINED RELEASE ESTROGEN VAGINAL RING PESSARY FOR TREATMENT OF ATROPHY, CYSTITIS AND UTEROVAGINAL PROLAPSE

FIELD OF THE INVENTION

The present invention relates to devices and methods for treating prolapsed pelvic organ, cystitis and Atrophy in women. Particularly, the invention relates to drug loaded vaginal support devices and methods wherein the device is inserted in vagina to support as well as release the drug. Specifically the invention relates to estrogen loaded vaginal pessary for alleviation of Pelvic Organ Prolapse (POP), Atrophy and cystitis in women. Particularly the invention relates to Sustained release Estriol vaginal pessary and its method of manufacture.

BACKGROUND OF THE INVENTION

Vaginal prolapse, medically termed as pelvic organ prolapse (POP) occurs when organs like the rectum, bladder or uterus drops down and either protrudes from or exerts pressure against the vagina. The organs within a women's pelvis are normally held in place by ligaments and muscles known as the pelvic floor. If these are weakened, the pelvic organs can bulge (prolapse) from their natural position in the Vagina. The most common cause of prolapse include; loss of oestrogen hormones at menopause; childbirth; being overweight; and chronic illnesses, such as chronic lung disease. Prolapse can also be worsened by the loss of muscle tone commonly associated with aging.

The two forms of treatment currently available to women suffering from pelvic organ prolapse includes: (i) Pessary's and (ii) surgical intervention.
  (i) Pessary's are the safer more affordable option traditionally used to treat pelvic organ prolapse. A pessary is a prosthetic device that is inserted into the vagina to support the internal structure, and to prevent further prolapse. The pessary will usually be inserted by a medical professional in an initial fitting.
  (ii) Surgical intervention i.e. Sacrocolpopexy or sacrospinous fixation—when the top of the vagina is attached to a bone or ligament. Pelvic floor repair, this involves surgical intervention where the vagina walls are tightened in support of the pelvic organs. Vaginal hysterectomy, which involves removal of the womb, this is a form of surgical intervention that tends to occur alongside pelvic floor repair.

There are currently two types of pessaries that are used in treating POP; (i) support and (ii) space-occupying pessaries. Support pessaries such as the ring pessary are typically used in treating stage I and stage II prolapse. Support pessaries are usually more convenient and comfortable then Gellhorn and other types of space-occupying pessaries used to treat advanced POP, which tend to be more difficult for patients to remove and reinsert. It may be of interest to utilise current technologies, in specific 3D printing, to design customised pessaries which not only support all stages of prolapse but are convenient and comfortable for individual patient use.

Oestrogen cream is commonly used to treat atrophic vaginitis, a disease that affects up to 50% of postmenopausal women. Atrophic vaginitis is a disease that results from a deficiency of oestrogen leading to vaginal dryness, burning, dyspareunia, vulvar pruritus, and discharge. If not treated this condition can be further agitated through the insertion of a pessary. Vaginal oestrogen cream is usually self-applied by women experiencing post-menopause. However, studies have been conducted into looking at alternative methods of administering oestrogen in post-menopause women. A study conducted by Hosseinzadeh, Ghahiri, Daneshmand & Ghasemi (2015) looked comparatively at vaginal oestrogen cream and sustained-release estradiol vaginal tablets in the treatment of atrophic vaginitis, where findings indicated that both methods of administration had the same efficacy as defined by the alleviation of symptoms, the main difference was found in the user experience. Users found that the tablet was significantly better regarding hygiene (0% hygiene issue tablet vs 23% hygiene issue cream) and a significantly easier method of treatment (90% tablet vs 55% cream; P<0.0001). Other studies found similar results, where the safety and efficacy of continuous low dose oestradiol released from a vaginal ring were tested in comparison to oestrogen vaginal cream. The results from this study also showed equivalence between both methods of administration in efficacy and safety, where the disparity was found in user experience, where patients found the vaginal ring to be the preferred and more acceptable option to the cream.

Women suffering from menopause related pelvic organ prolapse, are usually prescribed with Ovestin vaginal oestrogen cream, which is applied inside of the vagina by the patient. Ovestin, is a hormone replacement therapy used to counter the symptoms imposed by a shortage of oestrogen, which include; vaginal dryness, burning, pruitus, irritation and dysparenuria. Use of Ovestin cream is particularly important when treating menopause induced pelvic organ prolapse, mainly to prevent irritation and damage to the vagina when using pessary's. The idea proposed has two modifications to traditional pessary's: (i) adding a slow release oestrogen ring to the pessary device, effectively eliminating the need for patients to apply Ovestin and (ii) 3D-printed pessary's customized to the patient's internal vaginal structure.

Vaginal atrophy (atrophic vaginitis) is thinning, drying and inflammation of the vaginal walls that may occur when your body has less estrogen. Vaginal atrophy occurs most often after menopause. Treatment encompasses prescribing Vaginal moisturizers, like a vaginal moisturizer (K-Y Liquibeads, Replens, Sliquid, others) to restore some moisture to the vaginal area. Water-based lubricants. These lubricants (Astroglide, K-Y Jelly, Sliquid, others), Topical estrogens like Vaginal estrogen cream (Estrace, Premarin), Vaginal estrogen suppositories (Imvexxy), Vaginal estrogen ring (Estring, Femring), wherein the ring releases a consistent dose of estrogen while in place and needs to be replaced about every three months, Or prescribing Vaginal estrogen tablet (Vagifem), other modes comprises Systemic Estrogen therapy, usage of vaginal dilators, and topical Lidocaine.

CN109248139A discloses levonorgestrel vaginal rings that releases drug over a period of 21 days and comprises of Nusil MED silicone rubber.

CN104546668A discloses a vaginal ring comprising of liquid silicone rubber selected from silicone series Nusil u.s. MED company according to claim 1, release-controlling material is selected from silicone rubber from u.s. Nusil MED series, and u.s. Dow Corning medical grade silicone rubber C6 and the Q7 series for the delivery of drugs ranging from indomethacin; imidazole antifungal butoconazole nitrate, metronidazole; purine nucleoside antiviral acyclovir, ganciclovir; for contraception, hormone replacement therapy and the treatment of gynecologic diseases drug drospirenone progestogen, mifepristone, cyproterone, gestodene and estrogen drugs ethinyl estradiol, such as estradiol for over a period of 21 days.

EP0253109B1 discloses invention concerns an intravaginal device comprising a combination of 17 beta-estradiol and a supporting matrix for treating hypoestrogenic women. The device releases continuously 17 beta-estradiol at a rate of about 0.5 to about 25 mu g/24 h. The invention also comprises a method of preparing the device and a method of treating hypoestrogenic women by using the device. The invention released 20 pg/24 h of estradiol for a period of 150 days, these rings comprised of unmedicated outer, 1.5 mm thick layer of silicone tubing and a core having a diameter of 6 mm. The release rate during the 150 days period of time was fairly constant, but the rate does tend to decrease slightly with time. The content of estradiol was 4.79 mg/ring and of Silastic®.

WO2015073177A1 a therapeutically effective amount of estradiol, a solubilizing agent comprising a medium chain oil, and the pessary comprises about 1 μg to about 25 μg of estradiol and is a once a day formulation for treatment of vaginal atrophy.

EP2799042A discloses a vaginal ring for sustained release of dehydroepiandrosterone (DHEA), dehydroepiandrosterone sulfate (DHEA-S) or pharmaceutically acceptable upto a period of 30-60 days. The invention claims the vaginal ring for treatment of symptoms of vulvar and vaginal atrophy in postmenopausal women and sexual dysfunction in postmenopausal women.

WO9922680 A1 discloses a pessary (10) for treating uterine prolapse, and incontinence includes a medicated cartridge (14) that dispenses a sustained, steady dose of a drug. The drug comprises of an estrogenic composition that is released over a period of 30-60 days.

US20190358243A1 method for treating the symptoms of vulvo-vaginal atrophy (VVA) comprising: administering a vaginal suppository comprising 4 tg to 25 tg of estradiol, wherein the administration is conducted daily for two weeks, and twice weekly thereafter.

Currently available marketed products for vaginal estrogen are Premarin cream, Vagfem tablets, Estrace Cream, Osphena tablets (Oral SERM) and Estring Ring (Vaginal Estradiol Ring, 2 mg estradiol with 7.5 mcg release daily). Estring is the marketed vaginal ring formulation of Estradiol that releases the drug over a period of 90 days. A vaginal ring of core design, made from Silastic, measuring 9 by 55 mm, is currently marketed as Estring (Q Pharma AB, Malmo**, Sweden) in the United Kingdom, Europe, and North America. It is indicated for urogenital symptoms and does not relieve vasomotor symptoms. The ring contains 2 mg of micronized 17β-estradiol releasing 6.5 to 9.5 mg of estradiol daily.

There is currently no marketed product or device for controlled delivery of Estrogen for beyond 90 days. Estring® also is for a 90 day release that is it has to be removed and replaced by a new ring at the end of 90 days or 3 months. It is a primary objective to provide a vaginal ring pessary of Estrogen for sustained release of drug for a period of 180 days, or 6 months. Further, there is no marketed drug product or implant or delivery system that can deliver Estrogen for a period of 6 months and that is therapeutically efficacious for treatment of uterovaginal prolapse that Estring or another marketed product does.

Accordingly there is a need for a vaginal ring pessary with slow release Estrogen for improved patient compliance and for the treatment of atrophy, Cystitis and uterovaginal prolapse because of reduced dosage frequency and elimination of need for a local topical application of hormone cream or gel.

OBJECT OF THE INVENTION

It is the primary object of the present invention to provide a vaginal pessary for alleviating pelvic organ prolapse, particularly atrophy, cystitis and uterovaginal prolapse.

It is another object of the present invention to improved patient experience—considering comfort, ease of use and quality of life.

It is another object of the present invention to provide a vaginal pessary comprising estrogen.

It is yet another object of the present invention to provide a vaginal pessary for sustained and controlled release of Estrogen for a prolonged period of 6 months.

It is another object of the present invention to provide a vaginal pessary for treatment of pelvic organ prolapse which eliminate risks surrounding non-compliance to Ovestin.

It is another object of the present invention to provide a vaginal pessary for treatment of pelvic organ prolapse with high patient compliance.

It is another object of the present invention to provide a vaginal pessary for treatment of pelvic organ prolapse and method of manufacture by 3D printing method.

It is yet another object of the present invention to produce a pessary device with slow-release estrogen with minimal side effects and reduced dosing frequency.

SUMMARY OF THE INVENTION

It is a primary aspect of the present invention to provide a vaginal pessary for alleviating pelvic organ prolapse, comprising, an annular rigid structure of estrogen homogenously distributed in polymer matrix, wherein the polymer comprises of silicone elastomer and the pessary when inserted in the vagina has a sustained and continuous release of the estrogen hormone for a period of up to 6 months.

It is another aspect of the present invention to provide a vaginal ring pessary, wherein the polymer matrix comprises of Liquid silicone rubber MED-4870.

It is another aspect of the present invention to provide a vaginal ring pessary, wherein the ratio of the Estrogen to polymer is 1-15 mg:100 mg.

It is another aspect of the present invention to provide a vaginal ring pessary, wherein the loading amount of Estrogen in the vaginal pessary is in the range of 175-2400 mg.

It is another aspect of the present invention to provide a vaginal ring pessary, wherein the polymer comprises of Part A and Part B silicone materials.

It is another aspect of the present invention to provide a vaginal ring pessary, wherein the ratio of part A to part B is 1:1 by weight.

It is another aspect of the present invention to provide a vaginal ring pessary, wherein the annular or ring structure of the pessary comprises of an outer diameter of 50-110 mm preferably an outer diameter of 63 mm, inner diameter in the range of 20-110 mm, and preferably 43 mm, cross sectional diameter in the range 9-11 mm, preferably 10 mm ring.

It is another aspect of the present invention to provide a vaginal ring pessary, wherein the pessary has a durometer of a durometer of 60-80, most preferably 70 and Tensile strength of about 1300-1600 psi, preferably 1500 psi and mechanical strengths in the range of 3490-4946 g.

It is another aspect of the present invention to provide a vaginal ring pessary, wherein the estrogen comprises of estrogen, estrone, estriol or estradiol.

It is another aspect of the present invention to provide a vaginal ring pessary, wherein the estrogen is preferably estradiol.

It is another aspect of the present invention to provide a method or process of manufacture of a vaginal ring pessary, comprising of steps:

mixing of the polymer part A and part B (1:1 by weight) by spread mixing, gradual addition of the Estrogen in powder form to the blended polymer mixer to yield a estrogen polymer blend, loading of the blend into a 3D printed mould to yield a vaginal ring or pessary; and curing of the estrogen polymer blend by exposure to temperature 160° C. for 10 minutes and overnight at room temperature, wherein the dimensions of the vaginal pessary comprises of 63 mm outer diameter (range 50-110), 43 mm inner diameter (range 20-110), 10 mm ring diameter (cross section range 9-11 mm), and wherein the ratio of weight of estrogen to polymer is in the range of 1:100-15:100 mg.

It is another aspect of the present invention to provide a vaginal ring pessary, wherein the estrogen comprises of estrogen, estrone, estriol or estradiol.

It is another aspect of the present invention to provide a vaginal ring pessary, wherein the method comprises inserting the vaginal ring of claim 1 into the vaginal cavity to release estrogen over a period of 6 months.

It is another aspect of the present invention to provide a method of treatment of pelvic organ prolapse, wherein the mammal is human.

It is another aspect of the present invention to provide a method of treatment of pelvic organ prolapse, wherein vaginal ring pessary is inserted in the vaginal region for alleviating pelvic organ prolapse or uterovaginal prolapse, cystitis and atrophy.

DETAILED DESCRIPTION OF THE INVENTION

Figure 1:
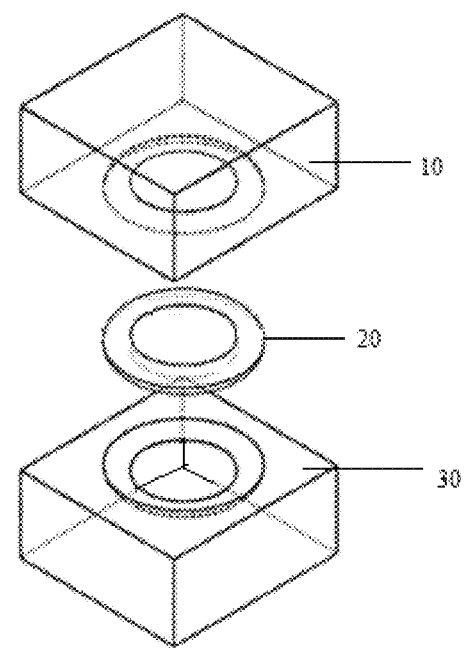
FIG. 1: A 63 mm pessary manufactured by 3D printed molding processing.

The present invention in an embodiment discloses a vaginal ring pessary for treatment of Pelvic Organ Prolapse or POP. As used herein, a "vaginal ring pessary" refers to a rigid body made up of polymeric material, which on insertion delivers drug or active agent to the vaginal and/or urogenital tract of a subject or patient at the vagina, cervix, or uterus. The invention is directed to the formulation and method of manufacture of a vaginal pessary which has rigidity and shore hardness and is inert in the physiological condition, and releases in a controlled and programmed manner the drug in the vaginal area.

The vaginal ring pessary is a vaginal device, particularly annular in structure. The annular ring may be prepared by a polymeric substance that provides enough rigidity, hardness and also provides drug release at the required release rate. Particular embodiment of the present invention provides a ring of dimensions appropriate for insertion into a female vaginal for controlled release of the dispersed active drug formulation. The API or active pharmaceutical ingredient may be dispersed or it may form the core of the device surrounded by the matrix for drug release by erosion.

Preferable embodiment of the present invention discloses a vaginal ring device [20] wherein the drug or the API is dispersed in the polymeric matrix which controls the release of the drug from the device to the subject over a selected prolonged period of time. Optionally an embodiment of the present invention may have the ring device [20] of shapes ring, an oval, an ellipse, a toroid, and the like.

The polymeric matrix according to an embodiment of the present invention comprises of an inert polymer. In some embodiments the matrix is an elastomer which is an amorphous polymer network formed when a polymer or a mixture of polymers undergo cross-linking. In further embodiments the matrix may be comprises a polysiloxane, a polyalkylene, a polystyrene, a polyvinyl acetate, a polyvinyl chloride, a polyester, a polyurethane, an acrylic, a nylon, a dacron, a teflon, or combinations thereof. In another embodiment of the present invention the polymeric matrix is silicone polymers. Particular embodiment of the present invention discloses the polymeric matrix as a matrix comprising Liquid silicone rubbers, or LSRs, which are elastomer systems reinforced with silica. Exemplary embodiments of the present invention comprises of silicone rubbers of Graded MED 4830 and MED 4870. Exemplary embodiments further discuss the choice of polymer based on the necessary hardness, tensile strength and Durometer values and their Fabrication methodology is discussed below.

Fabrication of Vaginal Ring Pessary for Controlled Release of Estrogen Over a Period of 6 Months or 180 Days.

Polymers chosen are NuSil MED-4830 and NuSil-4870. The polymers are liquid silicone rubber, specifically NuSil MED-4870 Liquid Silicone Rubber. They are specific for human implantation. Liquid silicone rubbers, or LSRs, are elastomer systems reinforced with silica. They contain functional polymers of lower average molecular weight and viscosity when compared to high consistency rubbers (HCRs). They are typically supplied as two-component systems Part A and Part B and formulated in a 1:1 mix ratio. Because their consistency is akin to petroleum jelly, they are often pumped with injection molding equipment to form molded components such as o-rings, gaskets, valves, seals, and other precision molded parts. The vaginal rings [20] are manufactured by 3D printing using moulds [10, 30] printed by nylon material.

Novel medicated and customised vaginal pessary rings [20] with different drug loadings were developed by using 3D printed moulds [10, 30]. Estriol was loaded in silicone solution and dispersed uniformly in the silicone matrix of the pessary device. That said, the specific aims of this study were: i) to incorporate estriol drug in silicone matrix; ii) to establish customised pessary device by 3D printed mould [10, 30]. iii) to analyse the interactions between drug and silicone polymers; and iv) to characterize and optimise the devices by studying the in vitro release profiles and morphology characters.

Materials and Methods
Materials

Estriol was purchased from Flem Pharma (Shanghai, China). Silicone (MED-4830 and MED-4870) was kindly gifted by Nusil™ (Carpinteria, United State). Potassium hydroxide (ACS reagent, >85%), calcium hydroxide (ACS reagent, ≥95.0%), urea (ACS reagent, 99.0-100.5%), D-(+)-Glucose (ACS reagent), glycerol (ACS reagent, ≥99.5%), lactic acid (meets USP testing specifications), acetic acid (ACS reagent, ≥99.7%), and hydrochloric acid (ACS reagent, 37%) were obtained from Sigma-Aldrich (Auckland, New Zealand). Bovine serum albumin (BSA, fatty acid free) was purchased from MP Biomedicals (Auckland, New Zealand). Simulated vaginal fluid (SVF) was prepared with two pH values (pH 4.2 for normal vaginal condition and pH 4.5 for menopause condition).

Physical Characteristics or Properties of the Polymer
MED-4870
Specific gravity—1.16 g/cc
Hardness—Shore A value—70
Tensile strength—5.17 MPa @ Strain 200%
Mix ratio of Part A:Part B is 1:1.
NuSil-4830
Specific gravity—1.13 g/cc
Hardness—Shore A value—30
Tensile strength—1,350 psi (9.31 MPa)
Cure time –5 minutes/150° C.
Mix ratio of Part A:Part B is 1:1.

Formulation of Ring:

The vaginal ring [20] is formulated by mixing of the part A and part B (1:1 by weight) of Polymers MED-4870 and MED-4830 by spread mixing. The polymers contain part A and part B that are blended together. Estrogen in powder form is gradually added to the polymer composition to yield estrogen polymer blend.

Curing of the estrogen polymer blend is performed at room temperature following exposure to temperature 160° C. for 10 minutes.

3D Printing:

The silicone blend was extruded through spreading mixing and then loaded into the 3D printed nylon mould by a metal spatula. The mould [10, 30] with silicone were placed in 160° C. oven for 10-20 min for curing resulting in the silicone was mixed well.

The molds [10, 30] were printed by nylon material.

Curing: The silicone blend extruded into the mold of the 3D printer and allowed a curing at 160° C. for 10-20 min.

Particularly the invention discloses in a preferred embodiment of the present invention a vaginal ring pessary [20] of Estrogen for sustained release of drug for up to 180 days or 6 months.

The invention is a vaginal pessary [20] as illustrated in FIG. 1 shows the view of a vaginal ring/pessary according to an embodiment of the present invention. The annular ring [20] is fabricated with dimensions in the range of 50-110 mm, preferably 60-80 mm and most preferably about 63 mm outer diameter. The range of inner diameter is in the range 20-110 mm and preferably 43 mm. The range of the cross sectional diameter is about 10 mm and the range is about 9-11 mm.

Exemplary embodiment of the present invention discloses a vaginal ring device [20] comprising an annular in structure with an outer diameter 63 mm, 43 mm inner diameter, 10 mm ring diameter (cross section).

Route of Administration

The vaginal ring is configured to be inserted into the vaginal cavity of a mammal, a human, particularly in the vaginal region of a female user or a patient and its fit and physical properties are evaluated to provide the necessary rigidity, and compliance to the patient to whom it is inserted in.

The present invention also includes a method of delivering one or more pharmaceutically active ingredients, according to an embodiment of the present invention to estrogens comprising estradiol, estrogen, estrone, estriol or estradiol. Inserting a ring pessary described herein into the vaginal cavity of a mammal, wherein the ring is retained for time sufficient to deliver the pharmaceutically active ingredient(s) to the mammal.

Exemplary embodiment discloses a vaginal ring pessary [20] which is a homogenous matrix comprising drug distributed in the polymer matrix. Here the drug is estrogen which is homogenously blended in the Liquid silicone polymer, selected from Nusil 4830 and Nusil 4870.

An embodiment of the present invention provides method of optimization of the Polymer for the fabrication of Vaginal Ring Devices.

Polymer Optimization

Preparation of Vaginal Ring Pessary [20] with Polymer MED-4830 comprising of steps:

Mixing of the polymer part A and part B (1:1 by weight) of Polymer MED-4830 by spread mixing;

gradual addition of the Estrogen in powder form to the blended polymer mixer to yield an estrogen-polymer blend; and curing of the estrogen polymer blend by exposure to temperature 160° C. for 10-20 minutes, wherein the ratio of weight of estrogen to polymer is 0.1 mg:100 mg by weight or 0.1% drug content.

Preparation of Vaginal Ring Pessary with Polymer MED-4870 comprising of steps:

Mixing of the polymer part A and part B (1:1 by weight) of Polymer MED-4870 by spread mixing;

gradual addition of the Estrogen in powder form to the blended polymer mixer to yield a estrogen polymer blend; and curing of the estrogen polymer blend at room temperature following exposure to temperature 160° C. for 10 minutes, wherein the ratio of weight of estrogen to polymer is in the range of 0.1 mg:100 mg of 0.1% by weight.

TABLE 1

Drug release over a period of 56 days in Simulated Vaginal Fluid

| S. NO | Polymer | Drug | SVF pH | Result ** % drug release | Weight of drug in mg |
|---|---|---|---|---|---|
| Trial 1 | MED-4830 | Estrogen (0.1% w/w) | 4.2 | 0.679% | 0.116 mg |
|  | MED-4830 | Estrogen (0.1% w/w) | 4.5 | 0.533% | 0.091 mg |
| Trial 2 | MED-4870 | Estrogen (0.1% w/w) | 4.2 | 0.850% | 0.152 mg |
|  | MED-4870 | Estrogen (0.1% w/w) | 4.5 | 0.840% | 0.170 mg |

Polymer Optimization.

Exemplary embodiment of the present invention has studied a 0.1% Estrogen drug content vaginal ring pessary fabricated with both MED 4830 and MED 4870 silicone rubber polymers.

Initial study was performed with both grades of Nusil silicone polymers. The table no. 1 provided above shows trial data for 56 days with the device weighing in the range of 16-21 g.

Drug Content in the Vaginal Ring Pessary:

Estrogen is loaded at a drug content/device of 0.1% w/w, equal to 17.0 mg (MED-4830) and 18.7 mg (MED-4870) per vaginal ring device.

Weight of the vaginal ring pessary: 17.0 g (MED-4830) and 18.7 g (MED-4870).

Drug content=0.1% by weight=17 mg to 18 mg for MED 4870.

Exemplary embodiment disclosed Estriol as the drug, the scope of the present invention should not be understood to be confined to Estriol alone but is applicable to estrogens in general.

TABLE 2

Comparative study for Drug Release of Nusil 4830 and Nusil 4870

| S. No | Silicone | Part A: Part B: Estriol (weight in mg)*** | Drug content (%)* | Results |
|---|---|---|---|---|
| 30-free | MED-4830 | 1:1:— | — | — |
| Trial 1 | MED-4830 | 1:1:0.002 | 0.1% | Over a period of 56 days, cumulatively released 0.679% (0.116 mg) and 0.533% (0.091 mg) in SVF of pH 4.2 and pH 4.5 respectively. |
| 70-free | MED-4870 | 1:1:— | — | — |
| Trial 2 | MED-4870 | 1:1:0.002 | 0.1% | Over a period of 56 days, cumulatively released 0.850% (0.152 mg) and 0.840% (0.170 mg) in SVF of pH 4.2 and pH 4.5 respectively. |

*: $drug = \dfrac{Mass\ of\ drug}{Mass\ of\ silicone}\%.$
**: SVF: simulated vaginal fluid
***: Part A and Part B: silicone materials which should be mixed at a fix ratio of Part A: Part B = 1:1.

An embodiment of the present invention discloses a comparative study of vaginal ring pessary comprising of 0.1% drug content for drug release. The vaginal rings fabricated from the two silicone polymers of grades MED 4830 and 4870 were studied for the release of the drug estrogen from the ring over a period of 56 days. The Control was fabricated without the drug.

In reference to FIGS. 4, 5, 6, 7 and Table 2 Cumulative Drug Release was studied using both the Polymers.

a) MED-4830 silicone films released in simulated vaginal fluid (SVF) of pH 4.2,
b) MED-4830 silicone films released in SVF of pH 4.5,
c) MED-4870 silicone films released in SVF of pH 4.2, and
d) MED-4870 silicone films released in SVF of pH 4.5;

Solid line represents 0.1% drug content (Code A), dotted line represents 0.5% drug content (Code B) and dashed line represents 0.1% drug content (Code C).

Trial Samples as illustrated in FIGS. 4, 5, 6, and 7.

Analytical Method

Estriol was analysed by high performance liquid chromatography (HPLC) using LC-20AT liquid chromatography LC-20AT HT auto sampler, DGU-20A5 degasser, RF-10A XL UV/VIS detector (Shimadzu USA manufacturing Inc, USA) equipped with a Phenomenex Synergi polar-RP 80A, 4.6×250 mm, 4 µm column. A mixture of acetonitrile: 0.1% formic acid in water (50:50) was used as mobile phase at a flow rate of 1 mL/min and injection volume of 10 µL with UV detection at 225 nm.

In vitro estriol release from silicone rings (IVIED-4830 and MED-4870) were studied in a simulated vaginal fluids (SVF) in pH 4.2 (normal vaginal pH) and pH 4.5 (post menopause vaginal pH) under sink conditions. Samples were accurately weighed and then placed in a screw top container containing 200 mL (for rings) SFV. All samples were shaken at 60 rpm at 35±2° C. At predetermined time intervals, 100 mL (for rings) of the incubation media from each sample was collected and an equal amount of fresh media was added into each release system to maintain the total volume and sink conditions. The concentration of estriol in the release media was determined by HPLC as described in the previous paragraph. The cumulative amount of estriol released was plotted against time for each sample. Estriol-free rings were used as controls. The experiment performed in triplicate with data presented as mean±SD.

Figure 3:
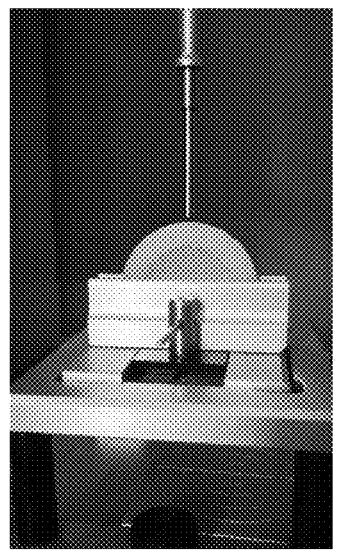
FIG. 3: Compression test in texture analyzer for the silicone rings
Figure 4:
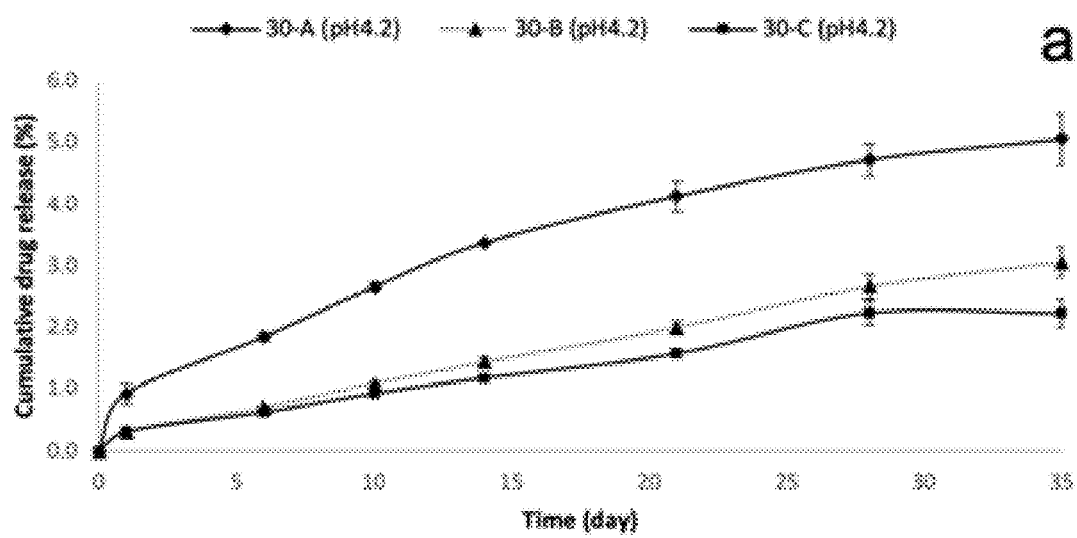
FIG. 4: MED-4830 silicone films released in simulated vaginal fluid (SVF) of pH 4.2.
Figure 5:
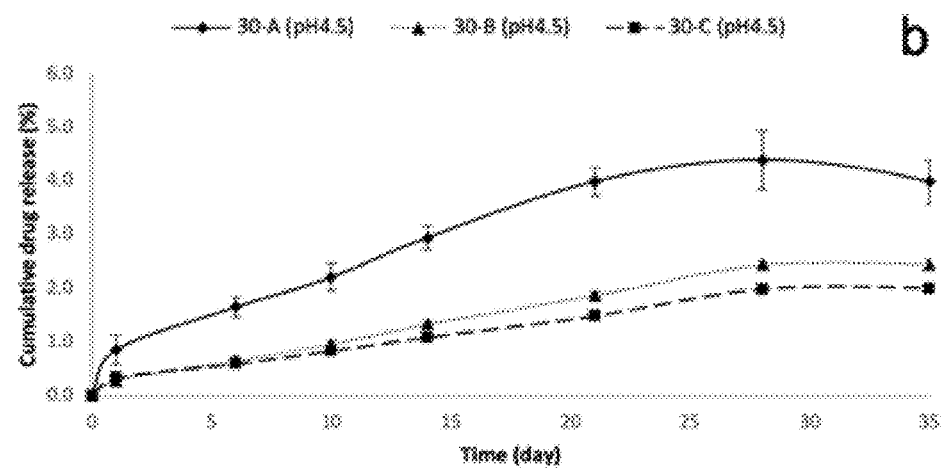
FIG. 5: MED-4830 silicone films released in SVF of pH 4.5.
Figure 6:
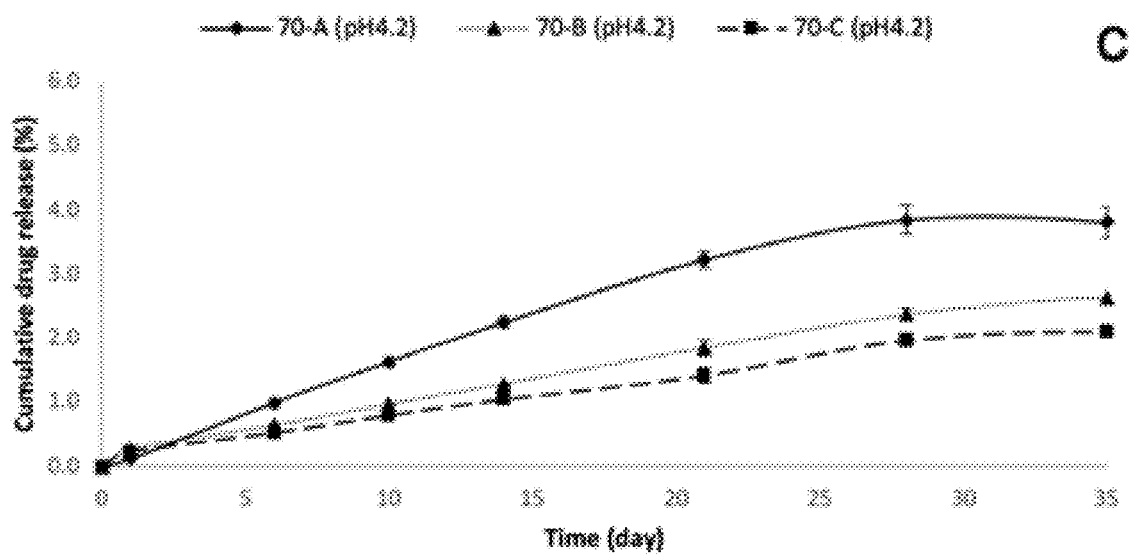
FIG. 6: MED-4870 silicone films released in SVF of pH 4.2.
Figure 7:
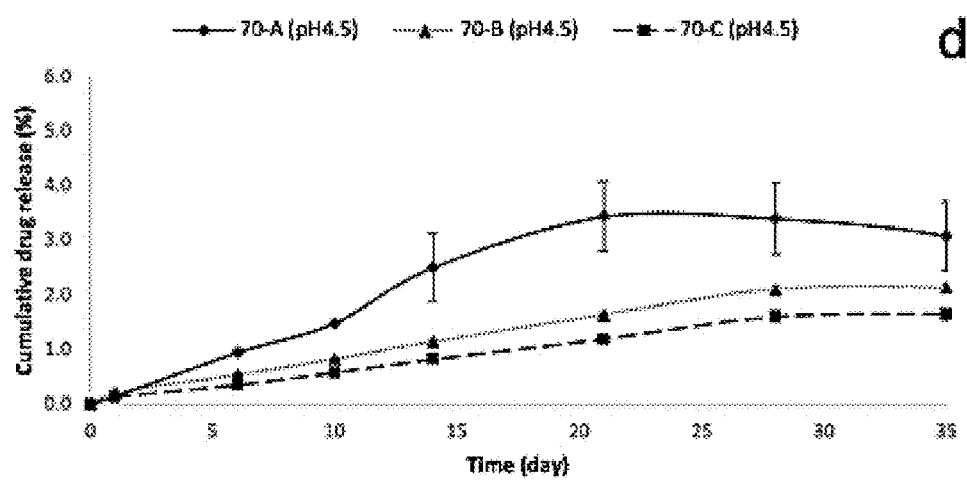
FIG. 7: MED-4870 silicone films released in SVF of pH 4.5.

As illustrated in FIGS. 4, 5, 6, and 7, cumulative release of silicone rings was presented in FIG. 3 (above), indicating that all formulations showed sustained release over a period of 56 days. The release behaviors were discriminated between different silicone materials and release conditions with different pH values. Over a period of 56 days, 0.68 and 0.53% of estriol (equal to 0.12 and 0.09 mg) were released from MED-4830 rings under pH 4.2 and 4.5 respectively; 0.85 and 0.84% of estriol (equal to 0.15 and 0.17 mg) were released from MED-4870 rings under pH 4.2 and 4.5 respectively.

Mechanical Test for Evaluation of the Ring Pessary

An embodiment of the present invention discloses the Mechanical Evaluation of the Vaginal Ring Pessaries [20] comprising two different Silicone Rubber Polymers of Grade MED 4830 and MED 4870.

TABLE 3

Trial Samples for Shore Hardness Test.

| Code | Silicone | Part A:Part B:Estriol (weight) | Drug content (%)* |
|---|---|---|---|
| 30-free | MED-4830 | 1:1:— | — |
| 30-A | MED-4830 | 01:00.0 | 0.10% |
| 30-B | MED-4830 | 01:00.0 | 0.50% |
| 30-C | MED-4830 | 01:00.0 | 1% |
| 70-free | MED-4870 | 1:1:— | — |
| 70-A | MED-4870 | 01:00.0 | 0.10% |
| 70-B | MED-4870 | 01:00.0 | 0.50% |
| 70-C | MED-4870 | 01:00.0 | 1% |
| 70-D | MED-4870 | 01:00.2 | 10% |
| 70-E | MED-4870 | 01:00.3 | 15% |

Figure 2:
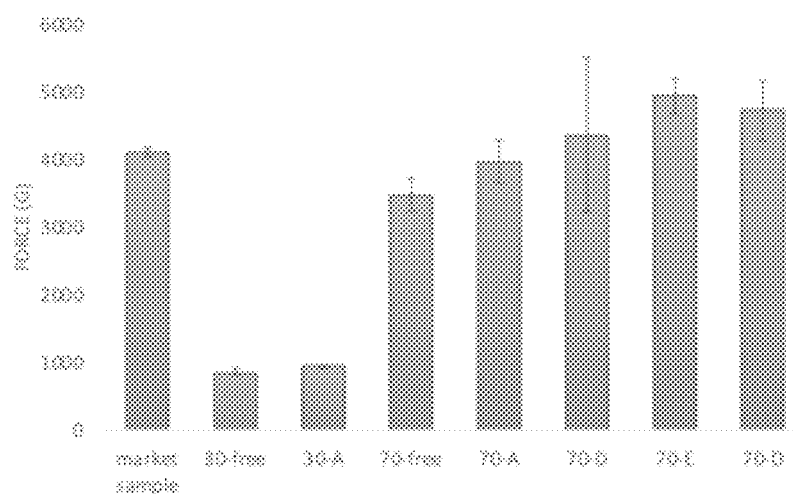
FIG. 2: Illustrating the Shore Hardness of the Vaginal Ring pessary

Shore Hardness Test: (FIG. 2, Table 3)

Compression test of the silicone rings were performed using a texture analyser (TA.XT2, Stable Micro System, Haslemere, Surrey, UK) by compression the ring for a distance of 10 mm (n≥3 compressions at different sites per ring) and the maximum compression force in each test was recorded (McCoy et al., 2019). Drug-free and drug-loaded rings were compared to identify if drug incorporation and its concentration can affect the mechanical property of the rings, illustrated in Table no. 3. Considering the rings are designed for long-term application, the rings treated with SVF for a period of 4-month at 35±2° C. were assessed to evaluate the change of mechanical strength during treatment. A commercial ring (brand/manufacturer) similar to the samples was also tested as a reference. Each ring was placed vertically on a ring holder fixed to the platform of the texture analyzer (as shown in FIG. 3). A probe attached to the movable arm was used to compress the ring at a distance of 10 mm at a speed of 2.0 mm/s and the maximum compression forces were recorded. Based on the results Polymer 4870 is chosen for the further vaginal ring pessary [20] device polymer optimization. Further embodiment of the present invention performed tests of mechanical strength on Ring fabricated with Polymer MED 4870 and results indicate the vaginal ring pessary has a durometer of 60-80, most preferably 70 and Tensile strength of 1300-1600 psi, preferably 1500 psi and mechanical strengths in the range of 3490-4946 g.

Final Ring Study

Example 1, 2 and 3 are the exemplary embodiments of the present invention with Vaginal Ring Pessaries [20] of different drug content and evaluated for the release of the drug after fabrication. Different Vaginal Rings with Drug Content 1% Estrogen, 10% Estrogen, and 15% Estrogen were studied for Drug release over a period 180 days.

Vaginal Ring Pessary Analytical Evaluation

In Vitro Release Studies

Different Vaginal Rings [20] with different Drug Content were studied for Drug release over a period 180 days.

In vitro Estriol release from silicone rings MED-4870 with different drug content (1%, 10% and 15% drug per device) were studied in a simulated vaginal fluids (SVF) in pH 4.2 (normal vaginal pH) and pH 4.5 (post menopause vaginal pH) under sink conditions. Samples were accurately weighed and then placed in a screw top container containing 200 mL SFV. All samples were shaken at 60 rpm at 35±2° C. At predetermined time intervals, 100 mL of the incubation media from each sample was collected and an equal amount of fresh media was added into each release system to maintain the total volume and sink conditions. The concentration of Estriol in the release media was determined by HPLC as described below. The cumulative amount of estriol released was plotted against time for each sample. Estriol-free films/rings were used as controls. The experiment performed in triplicate with data presented as mean±SD.

Analytical Method

1. HPLC method Estriol (E3) was analysed by high performance liquid chromatography (HPLC) using LC-20AT liquid chromatography LC-20AT HT auto sampler, DGU-20A5 degasser, RF-10A XL UV/VIS detector (Shimadzu USA manufacturing Inc, USA) equipped with a Phenomenex Synergi polar—RP 80A, 4.6×250 mm, 4 µm column. A mixture of acetonitrile: 0.1% formic acid in water (50:50) was used as mobile phase at a flow rate of 1 mL/min and injection volume of 10 µL with UV detection at 225 nm.

Example 1

Figure 8:
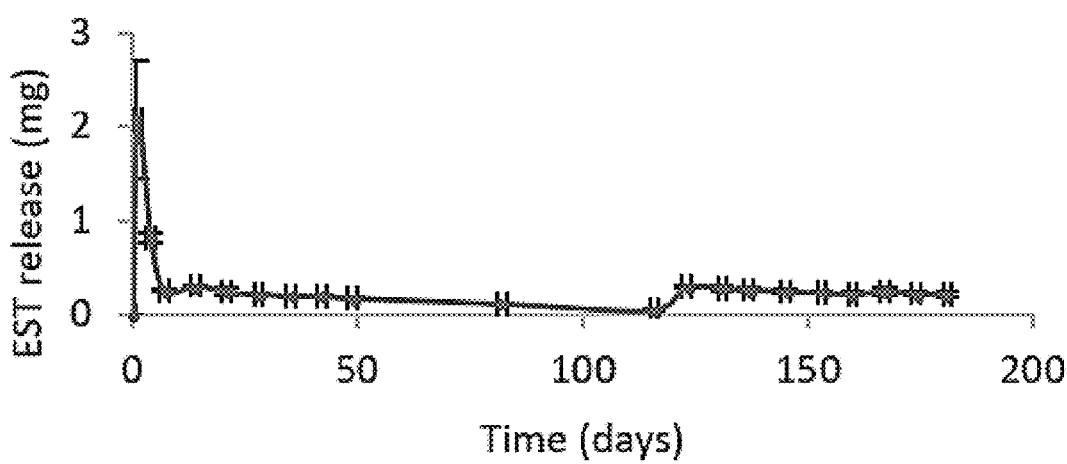
FIG. 8: Illustrates graph for EST release in mg Vs time in days upto 180 days for device with 1% EST in SVF pH 4.5.
Figure 9:
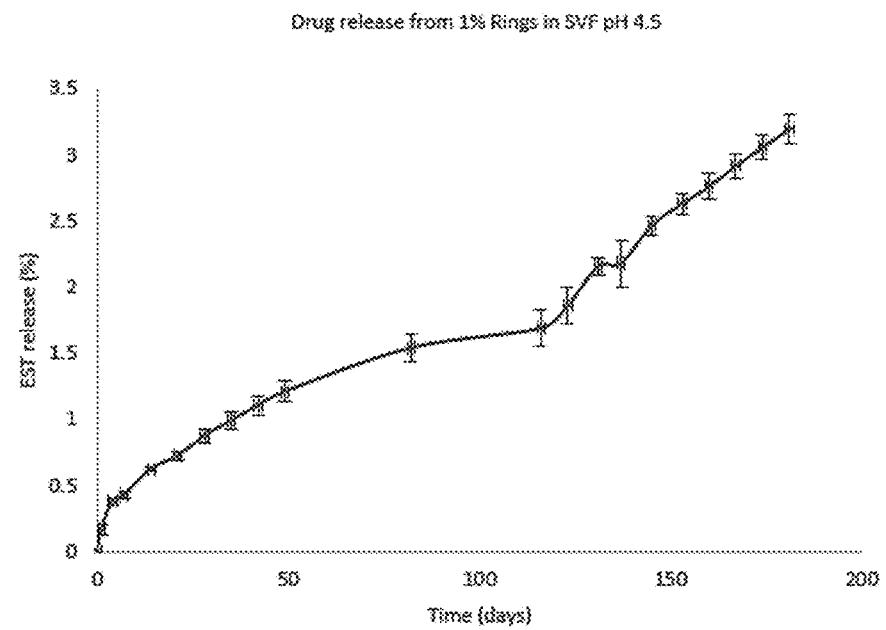
FIG. 9: Illustrates graph for % EST release Vs time in days upto 180 days for device with 1% EST in SVF pH 4.5.

Vaginal pessary or vaginal ring [20] is made up of Estriol as the drug with drug concentration of 1% w/w or 1 mg in 100 mg of polymer ie., in MED-4870. The drug release data is depicted in Table 4 and FIG. 8 and FIG. 9.

Vaginal ring pessary weight=16.0-18.5 g (Average weight 17.7 g)

Drug content=1% 175.7 mg/device, 10% 1747.7 mg/device and 15% 2361.1 mg.

TABLE 4

Drug Release from Vaginal Pessary with Estriol (1%) in MED-4870

| Days | Daily release (mg) | SD | Weekly release (mg) | SD | % Release | SD |
|---|---|---|---|---|---|---|
| 0 | 0 | 0 | 0 | 0 | 0 | 0 |
| 1 | 0.297 | 0.073 | 2.076993 | 0.624198 | 0.16833 | 0.038 |
| 4 | 0.116 | 0.005 | 0.815212 | 0.04668 | 0.380797 | 0.023 |
| 7 | 0.037 | 0.001 | 0.258378 | 0.005161 | 0.430795 | 0.027 |
| 14 | 0.044 | 0.001 | 0.310493 | 0.006401 | 0.623705 | 0.014 |
| 21 | 0.035 | 0.005 | 0.247287 | 0.041092 | 0.723877 | 0.034 |
| 28 | 0.031 | 0.002 | 0.220457 | 0.016307 | 0.874757 | 0.053 |
| 35 | 0.029 | 0.002 | 0.205023 | 0.013318 | 0.991792 | 0.062 |
| 42 | 0.029 | 0.002 | 0.199573 | 0.015249 | 1.105735 | 0.071 |
| 49 | 0.026 | 0.002 | 0.18229 | 0.01557 | 1.209959 | 0.078 |
| 82 | 0.018 | 0.001 | 0.122986 | 0.008711 | 1.541152 | 0.106 |
| 116 | 0.008 | 0.001 | 0.05366 | 0.0119 | 1.69076 | 0.137 |
| 123 | 0.043 | 0.002 | 0.30127 | 0.013402 | 1.862353 | 0.142 |
| 131 | 0.041 | 0.003 | 0.286207 | 0.026926 | 2.157096 | 0.067 |
| 137 | 0.039 | 0.003 | 0.271126 | 0.026697 | 2.182112 | 0.175 |
| 145 | 0.036 | 0.002 | 0.250556 | 0.014043 | 2.469305 | 0.072 |
| 153 | 0.034 | 0.002 | 0.238 | 0.014 | 2.632 | 0.078 |
| 160 | 0.032 | 0.003 | 0.224 | 0.025 | 2.763 | 0.097 |
| 167 | 0.036 | 0.004 | 0.251 | 0.036 | 2.918 | 0.091 |
| 174 | 0.033 | 0.002 | 0.232 | 0.020 | 3.059 | 0.095 |
| 181 | 0.032 | 0.003 | 0.226 | 0.028 | 3.198 | 0.110 |

Example 2

Figure 10:
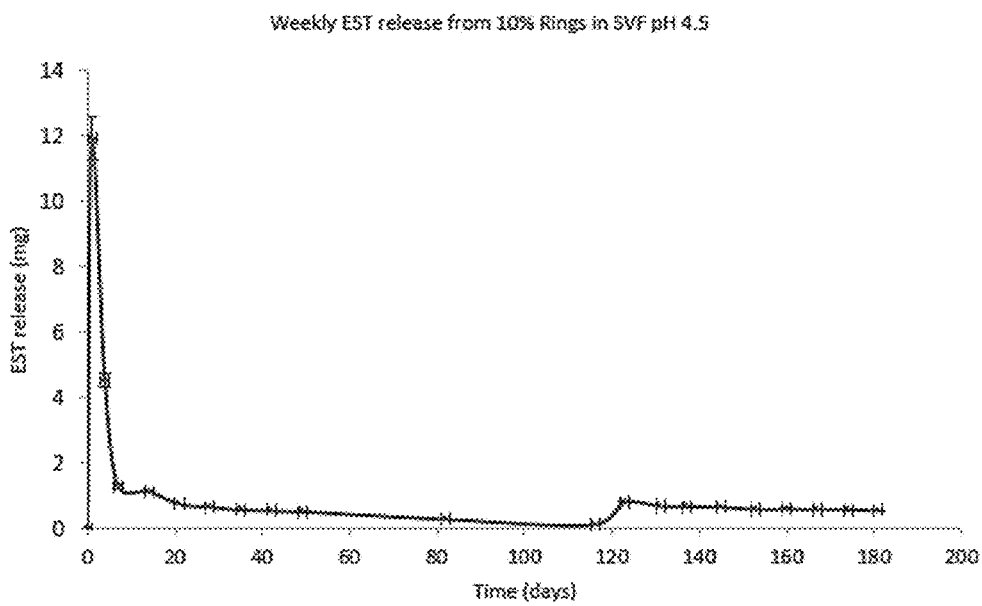
FIG. 10: Illustrates graph for EST release in mg Vs time in days upto 180 days for device with 10% EST in SVF pH 4.5.
Figure 11:
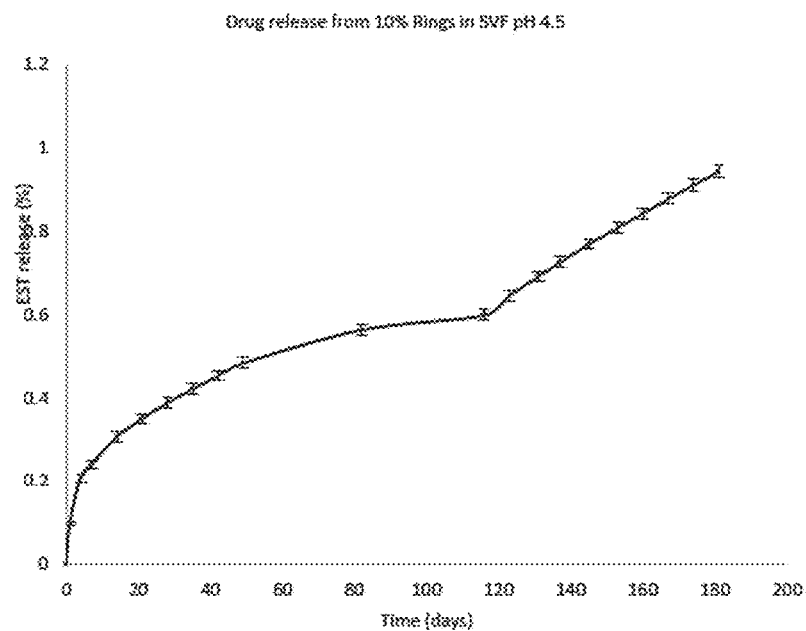
FIG. 11: Illustrates graph for % EST release Vs time in days upto 180 days for device with 10% EST in SVF pH 4.5.

Vaginal pessary or vaginal ring [20] is made up of Estriol as the drug with drug content of 10% w/w in MED-4870. The drug release data is depicted in Table 5 and FIG. 10 and FIG. 11.

TABLE 5

Drug Release from Vaginal Pessary with Estriol (10%) in MED-4870

| Days | Daily release (mg) | SD | Weekly release (mg) | SD | % Release | SD |
|---|---|---|---|---|---|---|
| 0 | 0 | 0 | 0 | 0 | 0 | 0 |
| 1 | 1.703 | 0.078 | 11.92016 | 0.664646 | 0.097447 | 0.004581 |
| 4 | 0.647 | 0.023 | 4.529327 | 0.197641 | 0.208533 | 0.008832 |
| 7 | 0.189 | 0.009 | 1.321577 | 0.076768 | 0.240945 | 0.010408 |
| 14 | 0.165 | 0.004 | 1.151873 | 0.034102 | 0.306865 | 0.012159 |
| 21 | 0.109 | 0.002 | 0.764833 | 0.013583 | 0.350635 | 0.012563 |
| 28 | 0.096 | 0.003 | 0.669373 | 0.028854 | 0.388937 | 0.011491 |
| 35 | 0.083 | 0.004 | 0.583187 | 0.03204 | 0.422304 | 0.012473 |
| 42 | 0.079 | 0.002 | 0.55338 | 0.016874 | 0.453974 | 0.012618 |
| 49 | 0.076 | 0.001 | 0.52909 | 0.011852 | 0.484254 | 0.012958 |
| 82 | 0.042 | 0.001 | 0.296795 | 0.006341 | 0.564309 | 0.01204 |
| 116 | 0.018 | 0.001 | 0.125799 | 0.006275 | 0.599283 | 0.01329 |
| 123 | 0.116 | 0.003 | 0.813573 | 0.027505 | 0.645835 | 0.012426 |
| 131 | 0.101 | 0.002 | 0.705918 | 0.017189 | 0.692004 | 0.012523 |
| 137 | 0.098 | 0.001 | 0.688539 | 0.011874 | 0.725775 | 0.012411 |
| 145 | 0.095 | 0.003 | 0.666668 | 0.023067 | 0.769375 | 0.012375 |
| 153 | 0.086 | 0.001 | 0.601 | 0.011 | 0.809 | 0.012 |
| 160 | 0.087 | 0.003 | 0.607 | 0.023 | 0.843 | 0.013 |
| 167 | 0.086 | 0.003 | 0.599 | 0.022 | 0.878 | 0.013 |
| 174 | 0.085 | 0.003 | 0.595 | 0.026 | 0.912 | 0.014 |
| 181 | 0.079 | 0.002 | 0.554 | 0.015 | 0.943 | 0.014 |

Example 3

Figure 12:
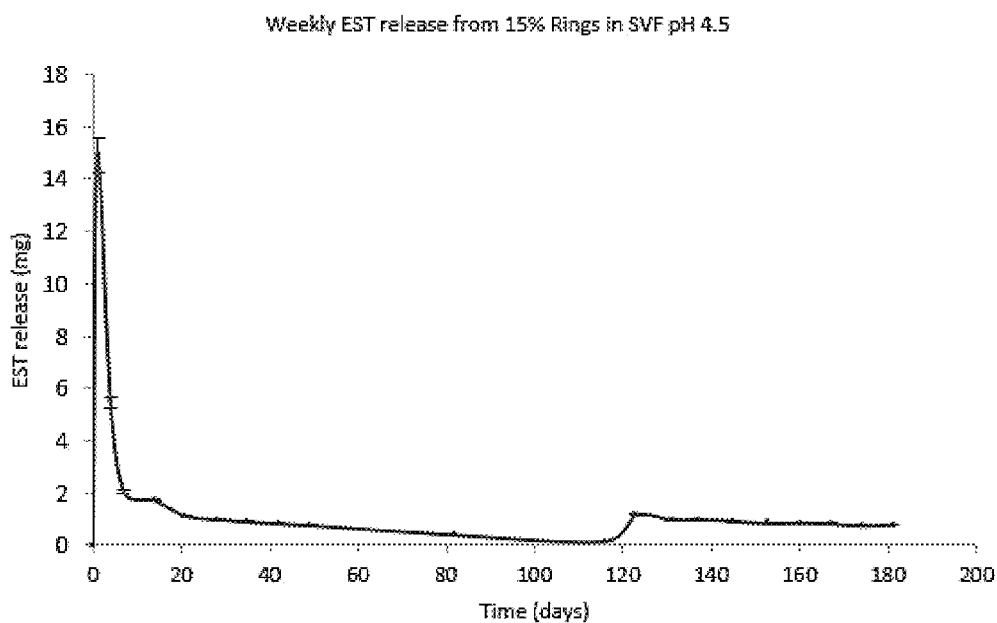
FIG. 12: Illustrates graph for EST release in mg Vs time in days upto 180 days for device with 15% EST in SVF pH 4.5.
Figure 13:
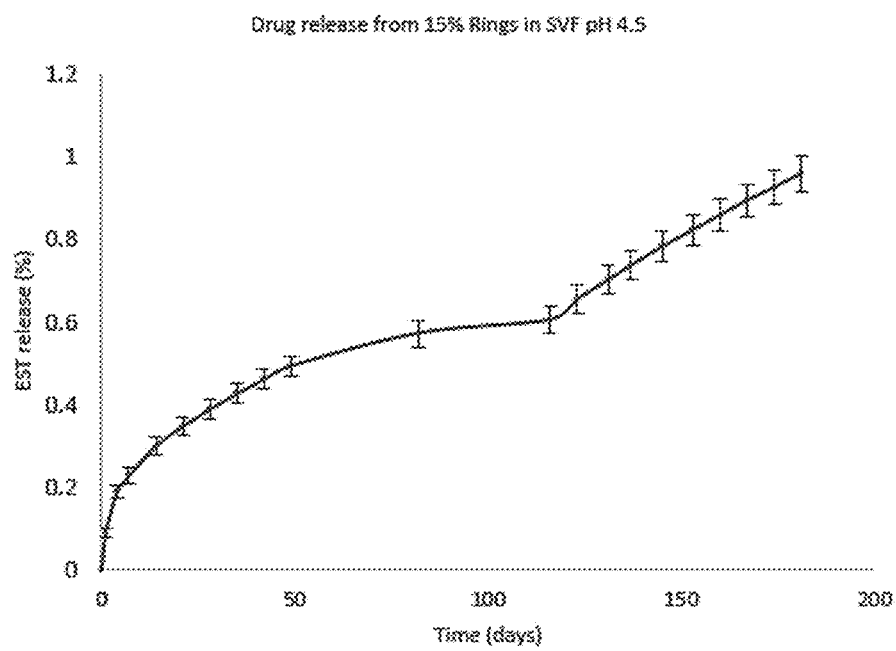
FIG. 13: Illustrates graph for % EST release Vs time in days upto 180 days for device with 15% EST in SVF pH 4.5.
Figure 14:
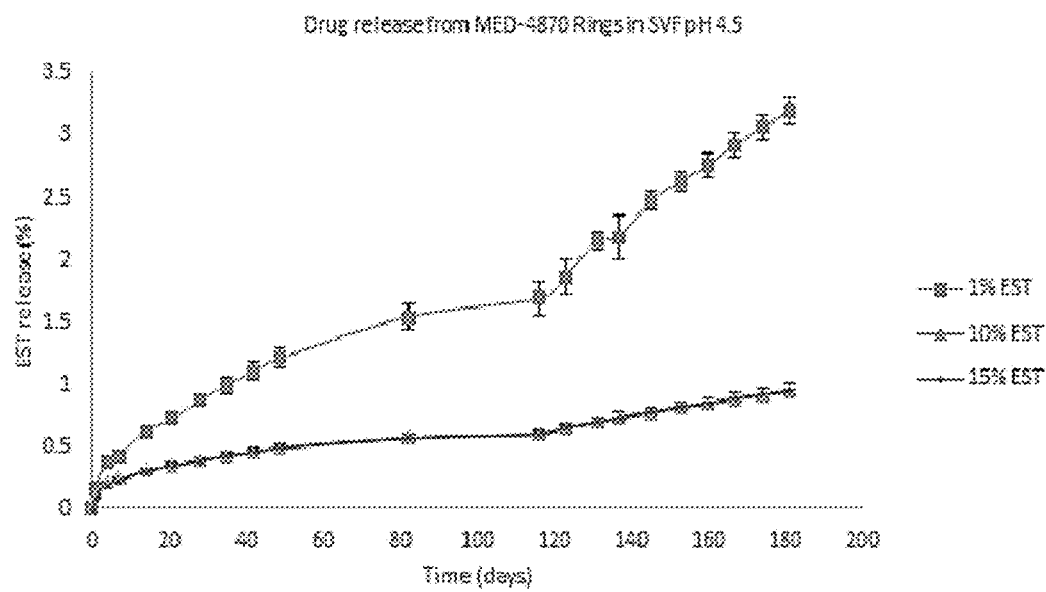
FIG. 14: Illustrates comparative graph of % EST release from vaginal ring device comprising 1%, 10% and 15% EST drug load.
Figure 15:
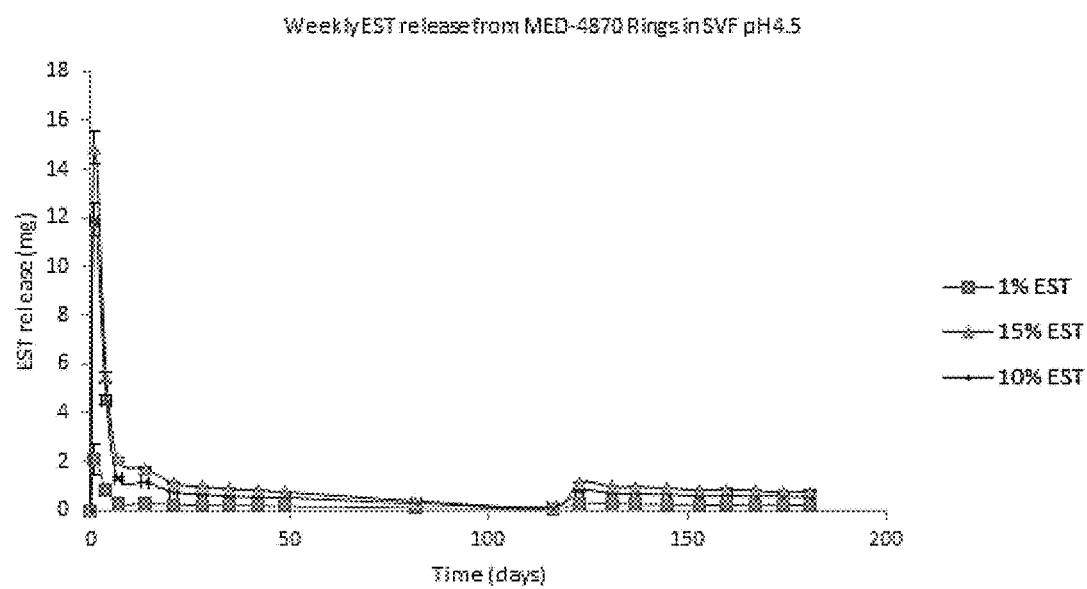
FIG. 15: Illustrates comparative graph of drug release in mg from the vaginal ring device comprising 1%, 10% and 15% EST drug load.

Vaginal pessary or vaginal ring is made up of Estriol as the drug with drug content of 15% w/w in MED-4870. The drug release data is depicted in Table 6 and FIG. 12 and FIG. 13.

TABLE 6

Drug Release from Vaginal Pessary with Estriol (15%) in MED-4870

| Days | Daily relaese (mg) | SD | Weekly release (mg) | SD | % Release | SD |
|---|---|---|---|---|---|---|
| 0 | 0 | 0 | 0 | 0 | 0 | 0 |
| 1 | 2.124567 | 0.194071 | 14.87197 | 1.663812 | 0.090239 | 0.010261 |
| 4 | 0.781012 | 0.023345 | 5.467086 | 0.200142 | 0.189673 | 0.015627 |
| 7 | 0.296129 | 0.027557 | 2.072902 | 0.236254 | 0.227359 | 0.01888 |
| 14 | 0.244034 | 0.010614 | 1.708237 | 0.090996 | 0.299759 | 0.021501 |
| 21 | 0.159404 | 0.008146 | 1.115827 | 0.06984 | 0.347009 | 0.021653 |
| 28 | 0.139904 | 0.00429 | 0.979327 | 0.036781 | 0.388501 | 0.022179 |
| 35 | 0.126696 | 0.003054 | 0.88687 | 0.026183 | 0.426125 | 0.023923 |
| 42 | 0.117984 | 0.001151 | 0.825887 | 0.009865 | 0.461135 | 0.024608 |
| 49 | 0.108698 | 0.002616 | 0.760883 | 0.022431 | 0.493392 | 0.02471 |
| 82 | 0.056592 | 0.004285 | 0.396147 | 0.036738 | 0.572688 | 0.032467 |
| 116 | 0.022561 | 0.001596 | 0.157928 | 0.013681 | 0.605149 | 0.031019 |
| 123 | 0.16542 | 0.006667 | 1.157937 | 0.057154 | 0.654269 | 0.033896 |
| 131 | 0.138733 | 0.002316 | 0.971127 | 0.019859 | 0.701331 | 0.034586 |
| 137 | 0.138838 | 0.001306 | 0.971868 | 0.011199 | 0.736652 | 0.035621 |
| 145 | 0.131821 | 0.000387 | 0.922746 | 0.003317 | 0.781367 | 0.036751 |
| 153 | 0.119 | 0.002 | 0.832 | 0.021 | 0.822 | 0.039 |
| 160 | 0.123 | 0.002 | 0.859 | 0.020 | 0.858 | 0.040 |
| 167 | 0.118 | 0.005 | 0.823 | 0.044 | 0.893 | 0.040 |
| 174 | 0.105 | 0.011 | 0.737 | 0.095 | 0.924 | 0.042 |
| 181 | 0.114 | 0.003 | 0.795 | 0.023 | 0.958 | 0.043 |

Results:

The vaginal pessary [20] releases the estrogen over a period of 6 months at a steady state release comprising 30-50 µg/day with a 1% drug content in the ring pessary, a 70-200 µg/day with a 10% drug content in the ring pessary and 100-300 µg/day with a 15% drug content per device.

The most preferred drug concentration is 1% and 10% for the vaginal ring pessary based on the results of drug release shown in Tables 4, 5 and 6.

Advantages:
1. Improved patient experience—considering comfort, ease of use and quality of life.
2. Eliminate risks surrounding non-compliance to Ovestin.
3. Cheaper to produce a pessary device with slow-release oestrogen as opposed to separate manufacturing of the cream and tubing.

At the outset of the description that follows, it is to be understood that the ensuing description only illustrates a particular form of this invention. However, such a particular form is only an exemplary embodiment and is not intended to be taken restrictively to imply any limitation on the scope of the present invention.

I claim:

1. A vaginal ring pessary for alleviating atrophy, cystitis and uterovaginal prolapse, comprising:
    an annular rigid structure of estrogen homogenously distributed in polymer matrix;
    wherein the polymer comprises of silicone elastomer and the pessary when inserted in the vagina has a sustained and continuous release of the estrogen hormone for over a period of 6 months; and
    wherein a ratio of the estrogen to the polymer matrix is 1-15 mg: 100 mg.

2. The vaginal ring pessary for alleviating atrophy, cystitis and uterovaginal prolapse as claimed in claim 1, wherein the polymer matrix is formed from a liquid silicone rubber.

3. The vaginal ring pessary for alleviating atrophy, cystitis and uterovaginal prolapse as claimed in claim 1, wherein the amount of Estrogen in the vaginal pessary is in the range of 175-2400 mg.

4. The vaginal ring pessary for alleviating atrophy, cystitis and uterovaginal prolapse as claimed in claim 1, wherein the annular or ring structure of the pessary comprises of a dimension 50-110 mm outer diameter.

5. The vaginal ring pessary for alleviating pelvic organ prolapse as claimed in claim 4, wherein the annular or ring structure of the pessary has an outer diameter of 63 mm.

6. The vaginal ring pessary for alleviating atrophy, cystitis and uterovaginal prolapse as claimed in claim 1, wherein the inner diameter of the ring is in the range of 20-110 mm.

7. The vaginal ring pessary for alleviating atrophy, cystitis and uterovaginal prolapse as claimed in claim 1, wherein the width of the ring, defined as one-half of a difference between the inside diameter of the ring and the outside diameter of the ring, is in the range of 9-11 mm.

8. The vaginal ring pessary for alleviating atrophy, cystitis and uterovaginal prolapse as claimed in claim 1, wherein the pessary has a durometer of 60-80.

9. The vaginal ring pessary for alleviating atrophy, cystitis and uterovaginal prolapse as claimed in claim 1, wherein the pessary has a Tensile strength of 1300-1600 psi, and mechanical strengths in the range of 3490-4946 g.

10. The vaginal ring pessary for alleviating atrophy, cystitis and uterovaginal prolapse as claimed in claim 1, wherein the estrogen comprises of estrogen, estrone, estriol or estradiol.

11. The vaginal ring pessary for alleviating atrophy, cystitis and uterovaginal prolapse as claimed in claim 1, wherein the estrogen is estradiol.

\* \* \* \* \*